United States Patent [19]

LeMay

[11] 4,010,370

[45] Mar. 1, 1977

[54] COMPUTERIZED TOMOGRAPHY APPARATUS WITH MEANS TO PERIODICALLY DISPLACE RADIATION SOURCE

[75] Inventor: Christopher Archibald Gordon LeMay, Osterley, England

[73] Assignee: EMI Limited, Hayes, England

[22] Filed: Nov. 11, 1975

[21] Appl. No.: 630,779

[30] Foreign Application Priority Data

Nov. 13, 1974 United Kingdom ............ 49074/74

[52] U.S. Cl. .............................. 250/366; 250/402; 250/445 T
[51] Int. Cl.[2] ................. G01N 21/34; G01N 23/04; G01T 1/20; H05G 1/00
[58] Field of Search .............. 250/445 T, 402, 366, 250/369

[56] References Cited

UNITED STATES PATENTS

| | | | |
|---|---|---|---|
| 3,778,614 | 12/1973 | Hounsfield | 250/366 |
| 3,852,605 | 12/1974 | Watanabe et al. | 250/402 |
| 3,940,626 | 2/1976 | Hounsfield | 250/366 |
| 3,949,229 | 4/1976 | Albert | 250/402 |

*Primary Examiner*—Alfred E. Smith
*Assistant Examiner*—T. N. Grigsby
*Attorney, Agent, or Firm*—Fleit & Jacobson

[57] ABSTRACT

Radiographic apparatus is described for evaluating the absorption coefficient of a body at each of a plurality of locations distributed over a planar slice disposed cross-sectionally of the body. A source is arranged to produce a fan-shaped, planar beam of radiation which is directed through the body, in the plane of said slice, and the source is orbited around the body about an axis perpendicular to the plane of said slice. Detectors are provided, and orbited in synchronism with the orbital motion of the source, each to detect the radiation emergent from the body along a plurality of paths. In order to render the paths substantially linear despite the orbital motion, a lateral scan is imposed upon the source which is sufficient, over a predetermined time period, to substantially cancel the orbital motion and replace it by a lateral motion.

7 Claims, 7 Drawing Figures

COMPUTERIZED TOMOGRAPHY APPARATUS WITH MEANS TO PERIODICALLY DISPLACE RADIATION SOURCE

This invention relates to a method of and apparatus for constructing a representation of the variation of absorption of a planar slice of a body with respect to penetrating radiation such as X- or γ- radiation.

One method of and apparatus for constructing such a representation is described in U.S. Pat. No. 3,778,614. According to one example given in that specification a scanning movement is imparted to a suitable source of radiation to provide a plurality of substantially parallel pencil beams of radiation at each of a plurality of inclinations in the plane of the slice. A suitable detector is scanned in a corresponding manner to provide a measure of the absorption suffered by each of the beams in passing through the body. These measurements of absorption are then processed by suitable means to provide a distribution of linear absorption coefficients for the planar slice. To provide the required plurality of beams the source and detector are reciprocated in the plane of the slice and orbited in steps about a common axis normal to that plane.

An alternative processing method involving a form of convolution is further described in United States Application No. 462,104 now U.S. Pat. No. 3,946,234.

In our co-pending United States Application No. 502,080 now U.S. Pat. No. 3,946,234 there is described a variation of the apparatus of the said British Patent, for the same purpose, having a source arranged to produce a fan shaped beam of radiation having a wide angular spread in the plane of examination. Collimators are provided to divide that beam into a plurality of pencil beams and an array of detectors is provided to detect the intensity of each of those pencil beams after passage through the body. Scanning motions as described are further imposed on the source-detector unit. As a result of the lateral scanning movement the array of detectors provides absorption information for a plurality of sets of parallel beams of radiation, the sets being angularly spaced by the angular separation of the beams. Thus the orbital step between each lateral movement is through a relatively larger angle. That variation of the apparatus is therefore capable of providing a faster scanning movement than that of the said British Patent. However for the examination of certain parts of the body it is desirable to further increase the scanning rate.

To that effect our co-pending United States Application Ser. No. 476,300 now U.S. Pat. No. 3,937,963 describes a method of and apparatus for constructing the said representation in which the angular spread of the fan shaped beam is sufficient to include the whole region of interest in the plane of the body so that a complete scan can be effected solely by orbiting the source and detectors about the common axis.

For both of the arrangements of the said United States Applications Ser. Nos. 476,300 now U.S. Pat. No. 3,937,963 and Ser. No. 502,080 now U.S. Pat. No. 3,946,234 for the orbital motion to be continuous rather than being stepped and occurring between determination of absorption. Unfortunately, however, such continuous motion results in data being obtained for beam paths which are distorted, as a result of motion in the course of a detector reading, and, in the case of the arrangement of United States Application Ser. No. 502,080 now U.S. Pat. No. 3,946,234, for sets of beam paths obtained in the course of a lateral scan which are not parallel as is desired but are distributed in the form of a fan.

It is an object of this invention to provide an improved arrangement allowing continuous orbital movement for the scanning methods of both of said applications.

According to the invention there is provided an apparatus for examining a substantially planar section of a body by means of penetrating radiation such as X- or γ- radiation including a source of a fan of radiation lying in the plane of the said section and originating substantially from a point, a plurality of detectors for detecting the radiation after passage through the body along a plurality of beams at different angles within the fan, means for angularly displacing the source and detectors about a common axis perpendicular to the said plane and means for subjecting the said point of origin to a periodic displacement, relative to the detectors and in the said plane, such that during each of a series of increments of said angular displacement, said periodic displacement causes a further angular displacement of said beams, substantially equal and opposite to said first mentioned angular displacement to cause each of said beams to remain parallel to its position at the start of the respective increment.

In order that the invention may be clearly understood and readily carried into effect examples will now be described with reference to the accompanying drawings of which.

Figure 1:
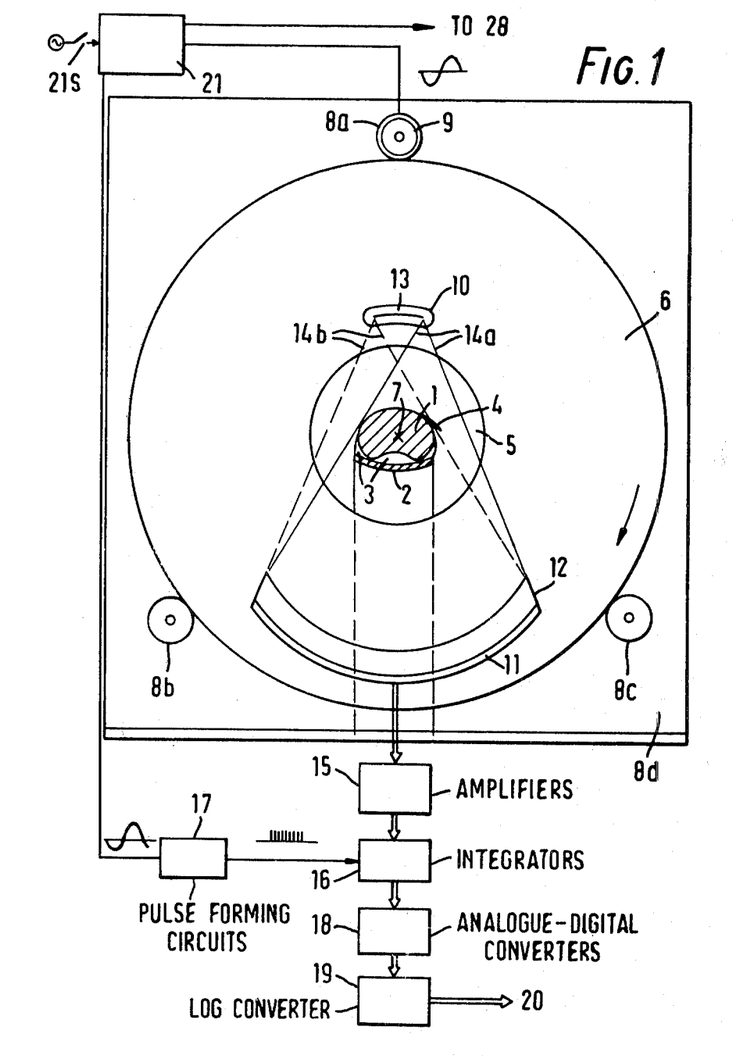
FIG. 1 shows one example of an X-ray apparatus incorporating an embodiment of the invention.

Referring to FIG. 1 there is shown therein an apparatus, of the type described in the aforesaid United States Application Ser. No. 476,300 now U.s. Pat. No. 3,937,963 incorporating one example of the invention. A body 1 to be examined, shown in transverse section, is supported on a suitably shaped bed 2, also shown in transverse section. A material 3, having an absorption to the radiation similar to that of body tissue, is positioned between the body 1 and the bed 2, to substantially exclude air from the gap therebetween, and is extended partly about the body to provide an approximately circular cross-section to the radiation. The body is retained firmly in the desired position by means such as a retaining strap 4. If desired a more rigid retaining ring, such as the two part ring described in co-pending United States Ser. No. 476,300 now U.S. Pat. No. 3,937,963 may be used.

The bed 2 and the body 1 are inserted into an aperture 5 in a rotatable member 6 so that a desired part of the body is centred in the aperture. The rotatable member 6 is arranged to rotate about an axis 7, longitudinal of the body 1 and perpendicular to the paper, central to the aperture 5. For that purpose it is supported by three gear wheels 8 *a,b,c*, which engage with gear teeth, not shown, cut into the periphery of member 6. The gear wheels 8 are journalled in a main frame 8*d* of the apparatus which may take any form suitable to support the apparatus and to allow the necessary rotation. Gear wheel 8*a* is driven by a synchronous electric motor 9, also mounted on the main frame, the operation of which will be described hereinafter.

The rotatable member 6 also carries a source of X-rays 10, a bank of detectors 11 and associated collimators 12. The detectors, which in a typical embodiment number 200, can be of any suitable type, for example scintillation crystals with associated photomultipliers or photodiodes.

The source 10 is of the type which includes an elongated target/anode 13, which will be discussed further hereinafter, and provides a fan shaped spread 14 of X-rays from a substantially point origin which can be scanned by electronic means from the position 14*a* to the position 14*b* shown. In this example the corresponding scan of the substantially point origin of the X-rays along target 13 is of the order of 10 cm although it may be less if desired. The collimators have longitudinal axes which intersect at the centre of the anode 13, the axes being angularly spaced by about 1/3° from each other.

In this example the X-ray source 10 is placed of the order of 40cm from the central axis 7 with the detector 11 being placed a further 80cm. on the opposite side of axis 7 so as to intercept the radiation of fan 14 for any position of the point of origin of the X-rays in its lateral scan along target 13. The detectors and source preferably lie along arcs of a single circle which, in this example, is not concentric with axis 7. It should be understood that collimators 12 are of dimensions which allow such interception while preventing the reception of scattered reception to the greatest degree practically possible. Although in the example the distance between source 10 and axis 7 is half of that between detector 11 and axis 7, the relationship is for the purpose of obtaining a particularly beneficial result which will be explained hereinafter. If desired the source and detectors may be placed equidistant from the axis or in any other desired relationship.

Disregarding for the moment the rotary motion referred to hereinbefore, the arrangement is such that the point of origin of the X-rays is scanned steadily along target 13, taking the fan of X-rays from 14*a* to 14*b*, and is rapidly returned to the starting point before repeating the scan. During the time of one such scanning movement each detector of array 11 provides an output indicative of the intensity of radiation incident thereon. These outputs are amplified in amplifier 15 and then input to integrators 16. There the outputs are integrated over periods determined by a series of pulses from pulse forming circuits 17. In this example the timing of the pulses is such that there are eleven integration periods in the time of one lateral scan of X-ray fan 14 from 14*a* to 14*b*. Thus each detector measures radiation in effect along eleven narrow beams joining that detector with eleven equally spaced positions along target 13. Hereinafter the word beam will be used to denote a beam of radiation incident on a detector and scanned with the source and detectors.

Conversely the path through the body irradiated by a beam, and fixed in relation to the body, will be termed a beam path. The paths are, of course, of width determined by the integration intervals and are of a shape determined by the geometry of scanning movements in those intervals. For the purposes of illustration, however, they may be considered to be represented by single lines which are in fact their centre lines. The lines illustrating the extremes of fan 14 are in fact the centre lines of the extreme beams of the fan. Signals representing the intensity of radiation received along such paths are converted to digital form in converters 18 and to logarithmic form in converters 19 for output at 20 for further processing. It will be understood that one amplifier 15, integrator 16. A/D converter 18 and log converter 19 is provided for every detector, all operated in synchronism. The processing is effective to sort the signals into sets representing absorption along sets of parallel paths, as will be further explained hereinafter, for processing by a suitable method such as that described in our co-pending United States Ser. No. 462,104 to provide the desired representation. The circuits 15 to 19 are of well known construction.

In order to achieve the effect of the present invention, which will be described in detail hereinafter, motor 9 provides a continuous motion of rotatable member 6 and all the equipment mounted thereon, in the direction shown by the arrow about axis 7 and therefore about the body 1 of the patient on bed 2. The rotary motion and the lateral scanning of X-ray fan 14 must be in a strict relationship to achieve the desired result. Synchronous motor 9 is driven by a periodic sinusoidal voltage from a power supply 21 and, after a suitable period of time, stablises in synchronisation with that sinusoidal voltage. It will be appreciated that, when under load, the motion of motor 9 lags the phase of the sinusoidal voltage but this is not significant provided the load does not change and therefore the lag is constant. The sinusoidal voltage from supply 21 is supplied to a time base generator 28 (FIG. 2) where it provides a periodic sawtooth waveform voltage, to operate the scanning of source 10, and also to unit 17 which converts it to square pulses of the same phase and generates therefrom the series of pulses, in strict phase relationship with the sinusoidal voltage, to clear and read integrators 16 as explained hereinbefore. Pulse forming circuit 17 operates in a conventional manner by any suitable means known in the art. Flyback of the sawtooth waveform takes place during selected resetting periods of the integrators.

Figure 2:
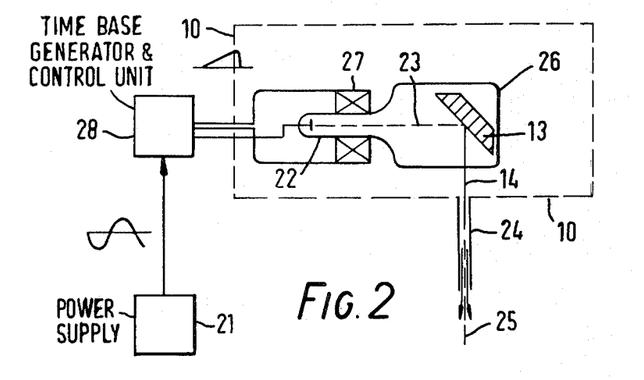
FIG. 2 shows an X-ray source suitable for use with the invention.

The X-ray source 10 is shown in greater detail in FIG. 2 and in this example comprises an electron gun 22, powered by a conventional supply not shown, providing a beam of electrons 23 which is incident on target/anode 13 to provide X-ray fan 14. In FIG. 2 the elongation of target 13 is perpendicular to the paper so that the X-ray fan 14 is also perpendicular to the paper. Source collimator 24 is provided, as shown, to restrict the X-rays substantially to the plane of the fan, shown dotted at 25 and that is then the plane of a section of the body 1 to be examined. The electron gun and target are enclosed in an evacuated envelope 26 having a neck section around which are disposed scanning coils 27. In operation, a suitable time (to allow motor 9 to settle in speed) after power supply 21 is switched on by switch 21*s* in FIG. 1, the time base generator 28 is switched on by a delayed signal from power supply 21. This signal also switches on electron gun 22. The sawtooth voltage from generator 28 scans the point of incidence of the electron beam 23 along target 13 from one end in a direction perpendicular to the paper to scan the X-ray point as shown in FIG. 1. Although a pencil beam of electrons is indicated it will be understood that it may be a ribbon shaped beam used in conjunction with a suitable shape of target 13. Furthermore oil cooling of target 13, although not shown, is preferably provided in conventional manner. Although scanning coils have been shown in FIG. 2, deflection plates may be used if desired; any configuration of source 10 capable of achieving the scanning of the X-ray fan 14 being suitable for use with the invention. Alternatively any other suitable arrangement for scanning the X-ray fan, in accordance with the principles outlined herein, may be employed.

As described hereinbefore, time base generator 28 provides the scanning sawtooth voltage in conventional manner in phase with the sinusoidal voltage provided by synchronous motor power supply 21 and this maintains the desired relationship between lateral scan and rotary motion. The exact relationship obtained is determined by the gearing of motor 9, turning member 6 through a predetermined angle for each cycle of the sinusoidal voltage. Since the sinusoidal voltage is also supplied to pulse forming circuits 17, the integration times are retained in the desired relationship with the scanning of X-ray fan 14 to provide the required effective beam paths.

It has been mentioned that processing, suitable for use with X-ray apparatus of the type described, such as that disclosed in copending U.S. Application 462,104 operates preferably on data representing the absorption along a plurality of sets of parallel beam paths in the plane of examination. The manner in which the present invention provides such data, despite the continuous orbital motion involved will now be described with reference to FIGS. 3 and 4.

Figure 3:
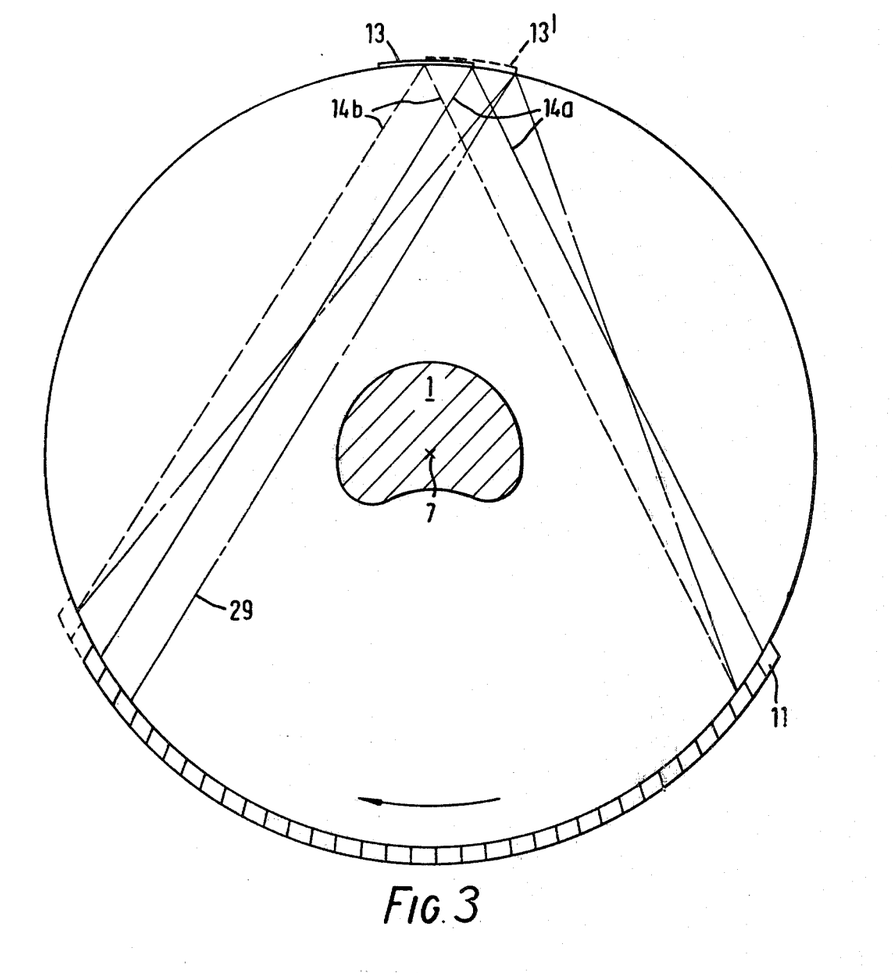
FIG. 3 illustrates the scanning movements of one example of the invention.

FIG. 3 shows in simplified form a scanning arrangement in which the detectors 11 and source anode 13 lie on the same circle, unlike the example of FIG. 1, and are therefore equidistant from axis 7. Thirty four detectors are shown for this simplified arrangement, it being understood that beam paths of radiation incident on those detectors will be represented by their centrelines. The source and detectors are illustrated at what may be considered to be an arbitrary starting position for the scan, at which the source spot of the X-rays is at the extreme right of anode 13 to provide fan 14a as in FIG. 1. Considering now the effect of the orbital motion and lateral motion of the X-ray source spot on anode 13 the relationship between them is arranged to be as shown by the broken lines. In the time in which the spot on anode 13 traverses from extreme right to extreme left of the anode the rotation of rotary member 6 brings anode 13 to the position 13' shown broken so that fan 14b emanates from a point, in relation to a fixed frame of reference such as body 1, which was initially at the centre of anode 13. The identical orbital motion is, of course applied to the detectors 11 taking them to the position of the broken lines so that each detector still intercepts the same beam of the fan 14. It will be observed that the two extreme bases of fan 14, and those intermediate but not shown have moved laterally but remain parallel to their original positions. Thus they provide two beam paths of the parallel set of beam paths required. In view of the chosen number of integration intervals, in the time of a lateral scan of the X-ray source spot, a further plurality of such parallel beams paths are provided between those shown.

As described hereinbefore the X-ray source spot is then subject to a rapid 'flyback' taking it to the extreme right of the anode at 13' to provide the fan of X-rays shown by the chain dotted line. The X-ray source spot is then at the position which it would have reached in the course of rotation, without the lateral scan, and is therefore inclined. It will be seen however that, while the extreme left hand beam takes a new inclination another beam, in this example the fifth from the left identified by reference numeral 29, takes up a position parallel to those previously taken by the extreme beam. A similar change applies to all other beams in the fan. In the course of the following lateral X-ray spot scan and orbital movement, the fan 14 moves to the position from which fan 14a originated but at the new inclination due to the intervening movement of detectors 11. In that time beam 29 moves to the position of the extreme left hand beam of fan 14a remaining at the same inclination as described hereinbefore. Thus beam 29 provides data for further beam paths of the parallel set started by the extreme left hand beam. In the course of further lateral scans of the X-ray source spot other detectors will contribute data to this, and other, parallel sets extending them, as required, completely across the region including body 1.

It will be observed that at junctions between parts of a parallel set, such as that between the paths examined by beam 29 and those examined by the extreme left hand beam, a path is examined twice by two beams. In practice, because of the finite time of a flyback of the source spot the two beams will not examine exactly the same path thus denying a valuable check between the sensitivities of the different detectors.

Figure 4:
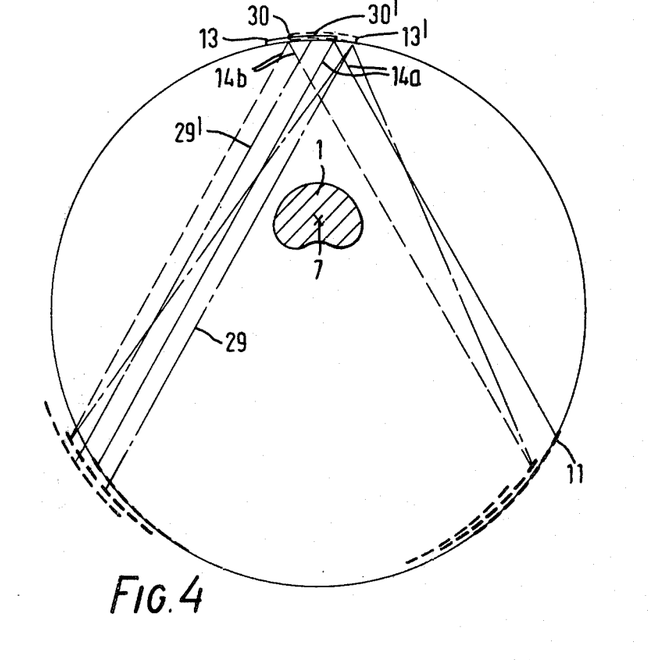
FIG. 4 illustrates the scanning movements of another example of the invention.

In order to provide the overlap, between portions of a parallel set provided by different detectors, which allows such comparisons between detectors, the preferred embodiment of FIG. 1 employs the unequal spacing of source and detectors which is shown in simplified form in FIG. 4.

In that Figure the arrangement has been shown to be substantially identical to that of FIG. 3 except that the source anode 13 and detectors lies on a circle which is not concentric with axis 7. The distance between axis 7 and the detector is then twice that between the axis and the source. In practice to provide clearance of the body 1 it is likely that the detectors would be moved to twice the radius of a FIG. 3 arrangement. However the difference from FIG. 4 would then merely be one of scale. The scanning motions of the FIG. 4 arrangement are substantially the same as those explained in relation to FIG. 3, the overlap being produced entirely as a result of the geometry adopted. In the course of the initial orbital motion the X-ray source spot is scanned from the extreme right to the extreme left of anode 13 to maintain the beams of fan 14 at the same inclination to the fixed frame of reference, despite the orbital motion, as explained hereinbefore. Since the detectors are at the same radius the angular motion to be compensated is substantially the same although in view of the off centre axis the detectors suffer a precession as shown. However, since the source anode 13 is now at half the radius it will not move through the same distance for the same angular change. Consequently instead of the source spot at the left hand end of the anode, at 13', being halfway along the initial position of the anode, as in FIG. 3, it is two thirds of the distance along that position, namely at position 30. As before a parallel set of data has been provided by the traverse and orbit combined. Of course source anode 13 also suffers from a precession, smaller than that of the detectors, which does not essentially affect the scanning motion used.

As before the spot 'flies back' to the extreme right of the anode, at 13', giving a new fan, indicated by the wide chain dotted lines and at a new inclination. Also as before one beam, 29 which in this case is the fourth from the left is parallel to the previous positions of the extreme lefthand beam and commences a new portion of the parallel set. However the spot now reaches the end of the anode two thirds of the way along position 13', namely at 30' to provide a beam along path 29' indicated by the fine chain dotted line, to the fourth detector which is displaced as shown. As before flyback follows this to start the next of the series of lateral scanning movements. It will be apparent however that the contributions to the parallel set between the extreme left hand beam paths of 14a and b are overlapped by those between 29 and 29'. Thus the sensitivities of, in this example, the first and third detectors on the left can be compared for all beam paths between 29' and the extreme left hand beam of 14a. The same is true for all other detectors of the fan and all other contributions to the parallel sets by further lateral scans of the source spot.

As for the FIG. 3 arrangement finite time flyback will prevent the full attainment of the overlap shown in the Figure but in this example overlap of several beams is still provided. In the course of many lateral source spot scans the arrangement provides that all beam paths, except some at extremes of each parallel set, are examined by two detectors and the detailed geometry may readily be adjusted to provide this despite the finite flyback time. It will be understood that, because of the steady precession of source and detector, caused by the off-centre axis, the beam paths described as identical will be different at the extremes near to source and detectors. However since they will be substantially identical in the region of the body 1 the conditions required are suitably satisified.

If required the source may be placed intermediate the positions of FIGS. 3 and 4. It will be apparent that placing the source of FIG. 3 at a slightly reduced distance from axis 7 will give sufficient overlap to negate the effects as that arrangement of the finite flyback time.

It will be seen from the arrangements of FIGS. 3 and 4 that many other arrangements, of source and detector positions, detector numbers fan spread angle etc. may be provided that the base principle of the invention is satisfied, namely that the lateral scan of the source spot is sufficient, over a predetermined number of integration intervals, to substantially cancel the orbital motion of the X-ray fan so that the orbital motion is replaced in effect by a lateral displacement.

It should be understood that the arrangement of FIG. 4 is simplified for the purposes of explanation although the relative radii of source and detectors correspond to the preferred embodiment of FIG. 1. The numbers and relative spacing of the detectors in FIG. 4 are not those of the preferred embodiments.

The geometry and the relationships of the two scanning motions of the apparatus are predetermined, although provision may be made to vary them if desired. Consequently the beam paths which will be examined by the detectors in the course of a complete scan are known in advance and are supplied to predetermined locations of a store, in this example a random access memory (RAM) store, in response to the signals, from timing circuits 17, which determine the integration intervals. Each location in the store, representing a beam path may be identified by a suitable co-ordinate system, such as $r$, defined as the distance of the beam path from axis 7 along a perpendicular to the path, and $\theta$, defined as the angle which that perpendicular makes with an arbitrary zero.

Figure 5:
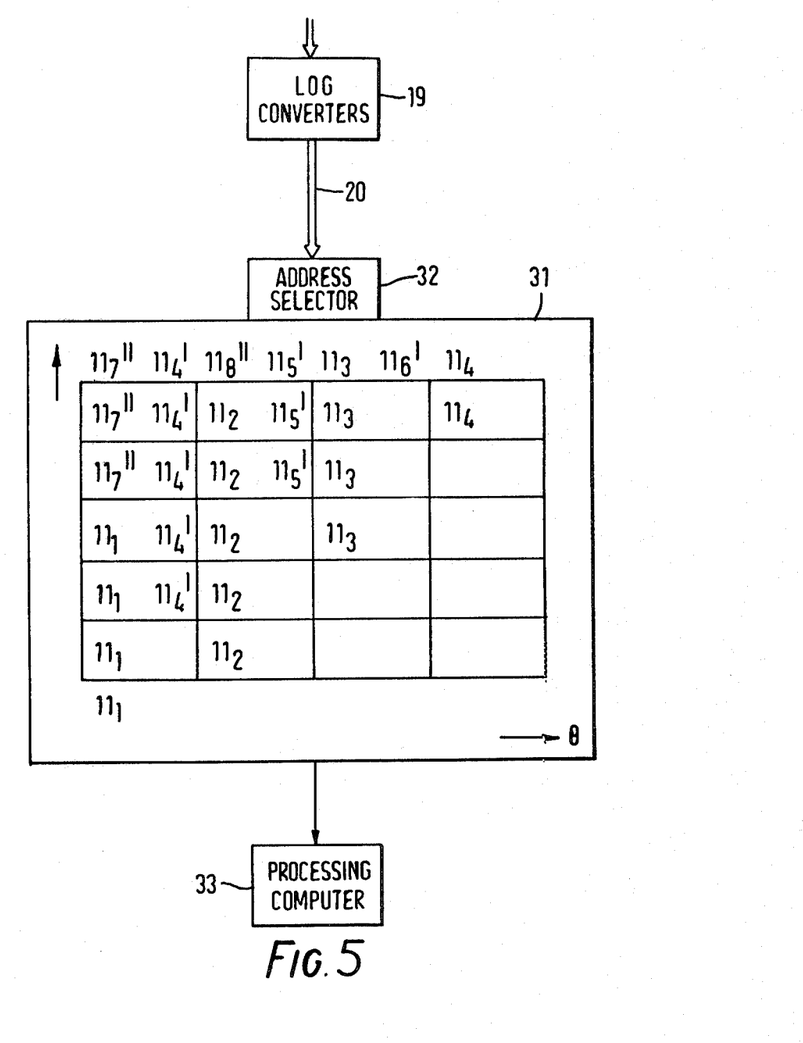
FIG. 5 is a diagram used to explain the organisation of data derived from the example of FIG. 4.

The store is indicated schematically at 31 in FIG. 5. The data supplied at 20 on individual circuit paths from log converters 19 are applied to an address selector 32 which, in response to the pulses from circuits 17 supplies them to the appropriate addresses in the predetermined sequence.

Within the box representing store 31 in FIG. 5 there is shown part of a matrix representing storage locations, each appropriate to a beam path and arranged in terms of the appropriate co-ordinates $r$ and $\theta$ for the purpose of illustrating the distribution of data. It will be understood, however, that the data need not, in practice, retain any particular physical distribution in store 31 provided the respective locations are known. For the purposes of illustration five integration intervals have been assumed for each lateral scan of the source spot, instead of the larger number used in practice. In view of the finite flyback time of the source spot a complete overlap is not achieved. The flyback time is, however, arranged to be equal to one integration interval so that the beams of successive parts of a parallel set are displaced by one exact beam path and remain in registration in the parts which do overlap. The data have been identified by the numbers of detectors 11 by which they are derived, the numbering starting at detectors $11_1$ at the extreme left in FIG. 4.

In the course of the first scan of the source spot detector $11_1$ provides data for five beam paths at constant $\theta$ but at decreasing $r$, for the co-ordinates chosen, and the data are read by address selector 32 into the appropriate five locations in succession as they are derived. Simultaneously the data for the other detectors are read into locations for other sets at constant $\theta$, displaced for those of $11_1$ as shown. Those for detectors beyond $11_4$ cannot be seen in the part of the storage matrix illustrated in FIG. 5. During the next scan of the source spot detector $11_4$ provides data for beam paths at the angle $\theta$ appropriate to paths previously examined by $11_1$ but starting at a higher value of $r$. These are also read into their appropriate locations in sequence, as indicated by $11_4'$. It will be seen that two of these locations already contain data for $11_1$. The new data are added to the previous data by any appropriate means, such as recirculation and adding of the previous data. Simultaneously data for the other detectors are read into the locations indicated by the primes. At the next lateral scan of the source spot a further change by three detectors, for a value of $\theta$, is made as shown by $11_7''$ and $11_8''$.

It will be observed that, as a result of the displacement of beam paths provided by the finite flyback time, each beam path will be examined by two detectors, with the exception of some at the end of the scan. In the absence of flyback delay, those beam paths in the region of overlap would have been examined by three detectors. The data for each beam path may merely be combined if desired. Data for these paths being examined only once may be doubled, discarded or their acquisition may be avoided by suitable tailoring of the strat and finish of the scan. Alternatively data added into an occupied location may be averaged with those already stored.

The provision of data for two detectors for each beam path allows the reduction of errors due to relative differences of sensitivities of adjacent detectors. Furthermore, since the detectors used change alternatively across a parallel set, differences across a parallel set tend to be smoothed out to the benefit of the finally derived representation. However, as a further refinement the fact that two detectors examine the same path, for which they should give the same value, allows the possibility of adjusting the gains of their respective amplifiers to equate their sensitivities. Such equalising may be carried right across the bank of detectors 11 by virtue of the successive overlaps.

At the conclusion of the complete scanning motions the store 31 contains data for a plurality of parallel sets of beam paths at different inclinations, as required for the aforementioned processing. These are then read out in sequence to a processing computer 33 for processing for example as described in co-pending United States Ser. No. 462,104 now U.S. Pat. No. 3,924,129.

It has been mentioned that the invention can also be used with an apparatus of the form described in co-pending United States Serial No. 502,080 now U.S. Pat. No. 3,946,234 to eliminate the stepping of the orbital motion described in that application. The arrangement described therein employs a fan of radiation of relatively narrower angle together with a mechanical lateral motion of source and detectors to scan the fan across the body to achieve a required number of beam paths. It will be apparent that such a lateral scan, considered in relation to the motion of a single beam of the fan merely imposes a motion at constant $\theta$. Thus the principle of the invention, that the scan of the X-ray source spot temporarily negates the change of $\theta$ imposed by the orbital motion, is not affected by the extra source-and-detector lateral scan. The description of the relationship according to the invention given hereinbefore is therefore still appropriate to this other form of the apparatus although the effects of the superimposed constant $\theta$ motion should be considered when allocating the derived data to their appropriate storage locations.

Figure 6:
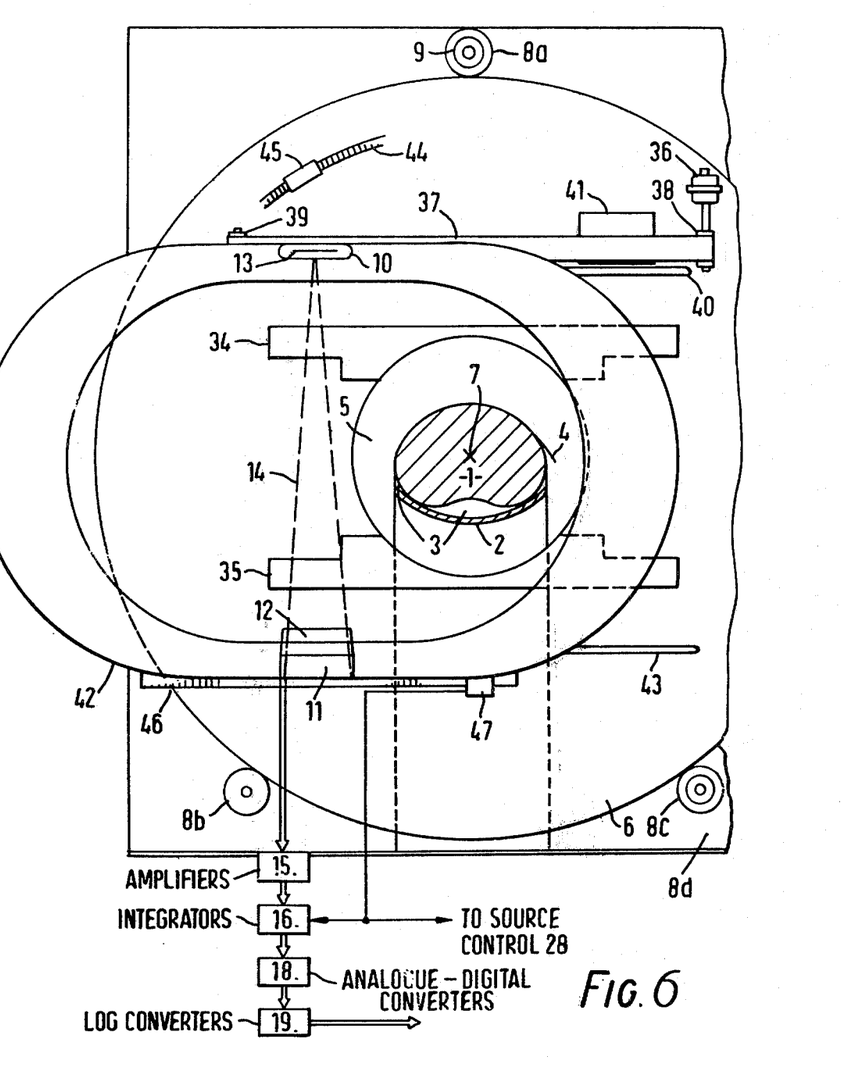
FIG. 6 shows another example of an X-ray apparatus incorporating an embodiment of the invention and FIG. 7 shows a simplified form of another embodiment of the invention.

There is shown in FIG. 6 an example of an apparatus according to the said United States Ser. No. 502,080 now U.S. Pat. No. 3,946,234 in which features common to the arrangement of FIG. 1 have been indicated by the same reference numerals. The rotary member 6, in this example, carries also two compensating members 34 and 35. These members are arranged to provide a substantially uniform absorption to the radiation for all beam paths of a source detector scan despite the substantially circular cross-section provided by the body 1. Thus it is ensured that any variations of absorption are caused substantially only by variations in the body 1. Such compensating members could also be provided for the FIG. 1 arrangement if desired.

Also secured to the member 6 is a reversible motor 36 which drives a toothed belt 37 by means of a drive shaft 38 journalled in member 6. The belt 37 also passes over an idler wheel 39 also journalled in member 6. Secured to the belt 37 is the source 10, which is of the type described hereinbefore. The source is driven to and fro laterally by the belt 37, being mounted on a bearing travelling in a track 40. A counter balance weight 41 is fixed to the opposite side of belt 37 to compensate for out of balance forces during the lateral movement.

Linked to the source 10 by a light weight but rigid yoke 42 is the collimator/detector unit 12/11. The detectors 11 and collimators 12 also move on a bearing on a track 43 on member 6.

As an alternative to the FIG. 1 arrangement for controlling the relative motions there is provided on turntable 6 a graticule 44 (only shown in part) comprising a translucent strip carrying engraved lines. The lines interrupt a light path between a light source and a photocell in unit 45 to provide pulses indicating the progress of the orbital movement. These pulses are used to cause periodic reversals of motor 36 is accordance with the required relationship. Yoke 19 carries a similar graticule 46 cooperating with light source and photocell unit 47 to provide signals indicative of the progress of the lateral scan of source 10 and detectors 11. These pulses are applied to the integrators 16 to control the integration intervals and to source control/time base generator 28 to control the scan of the source spot along anode 13 in the required relationship. The pulses may also be applied to a counter, not shown, to record the progress of the scan for the purpose of any processing or timing required.

It will be apparent that a photocell graticule combination could also be used to provide timing pulses for the FIG. 1 arrangement in which case pulses from a combination such as 44/45 monitoring the rotary motion would be applied directly to integrators 16 and source control 28.

Figure 7:
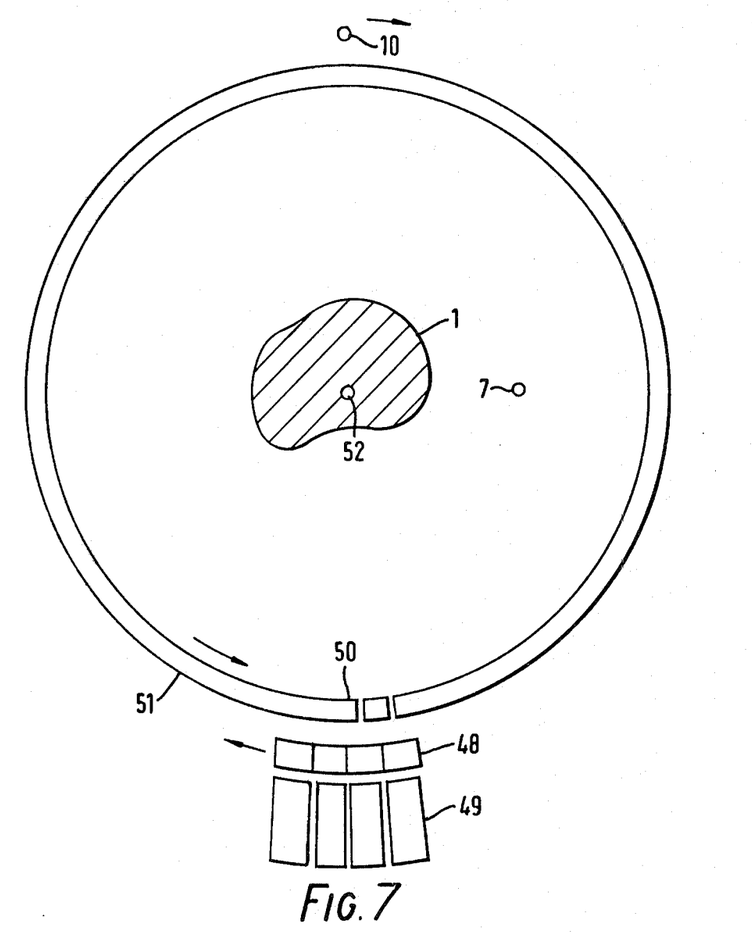

In a further embodiment of the invention FIG. 7 shows a means for obtaining the required motion of the X-ray beams without the use of a scanning anode X-ray source such as has been described hereinbefore.

In FIG. 7 the detectors 11 are shown in the form of individual scintillator crystals 48 and photomultipliers 49. The X-ray source 10 is in the embodiment a single point source of X-rays incident on the crystals 48. For simplicity only four typical detectors have been shown. A plurality of collimators 50 are provided on a ring 41 which rotates about an axis 52 which is fixed in relation to the source and detectors. In the case of an apparatus such as that shown in FIG. 1 axis 52 is identical with axis 7. However for an apparaus such as that shown in FIG. 6 these are not the same, as shown in FIG. 7, since axis 52 moves with the yoke 42.

Each collimator 50, of which only two are shown, is of a width suitable for defining a pencil beam, although in this embodiment each detector is significantly larger. The collimator ring 14 is arranged to rotate in the opposite direction to the rotation of the source and detectors and at such a speed that it matches the orbital motion of the source. Thus while each collimator passes across a detector it remains in a relationship with source 10 such that the pencil beam defined is subject to no rotation but a translational motion is substituted. It will be appreciated that this is the same effect described hereinbefore for the scanning anode source. As the collimator moves to the next detector the following collimator takes its place. Thus there is a sudden angular change corresponding to the flyback of the scanning anode source.

It will be appreciated that the collimators at the opposite side of the ring 51 can pass between the source 10 and the body 1. The ring 51 must, therefore, be slightly inclined in relation to the plane of the slice so that such interference is avoided.

It should further be noted that other collimators which are fixed relative to X-ray source 10 can be provided as close as possible to the body 1 so that as far as possible the body is not subjected to radiation which will not be accepted by collimators 50.

Alternatively collimators 50 may be placed so as to pass between the body and the source instead of between the body and the detectors. In that case the relative motion described would achieve the same effect, however the body would not be subject to radiation which is not to be detected.

What I claim is:

1. An apparatus for examining a substantially planar section of a body by means of penetrating radiation such as X- or γ- radiation including a source of a fan of radiation lying in the plane of the said section and originating substantially from a point, a plurality of detectors for detecting the radiation after passage through the body along a plurality of beams at different angles within the fan, means for angularly displacing the source and detectors about a common axis perpendicular to the said plane and means for subjecting the said point of origin to a periodic displacement, relative to the detectors and in the said plane, such that during each of a series of increments of said angular displacement, said periodic displacement causes a further angular displacement of said beams, substantially equal and opposite to said first mentioned angular displacement to cause each of said beams to remain parallel to its position at the start of the respective increment.

2. An apparatus according to claim 1 in which said source is an X-ray source incorporating an elongated anode arranged to provide X-rays in response to electrons incident thereon, said periodic displacement being the result of periodic displacement of said electrons on said anode.

3. An apparatus according to claim 1 wherein said source is disposed closer to said axis than said detectors.

4. An apparatus according to claim 3 wherein the distance between said source and said axis is subtantially half of the distance between said detectors and said axis.

5. An apparatus according to claim 1 including means for laterally displacing said source and said detectors in a common direction in said plane.

6. An apparatus according to claim 1 wherein in one of said increments one of said beams irradiates a series of beam paths at least some of which are substantially identical to beam paths irradiated by another of said beams in another of said increments.

7. An apparatus for examining a substantially planar section of a body by means of penetrating radiation such as X- or γ- radiation including a source of a fan of radiation such lying in the plane of the said section and originating substantially from a point, a plurality of detectors for detecting the radiation after passage through the body along a plurality of beams at different angles within the fan, means for angularly displacing the source and detectors about a common axis perpendicular to the said plane and means for periodically angularly displacing the said beams, relative to the said detectors and in the said plane, such that during each of a series of increments each of said beams remain at the same inclination in relation to said body for a predetermined lateral displacement.

* * * * *